US00PP23685P2

(12) United States Plant Patent
Bradford

(10) Patent No.: US PP23,685 P2
(45) Date of Patent: Jun. 25, 2013

(54) INTERSPECIFIC TREE NAMED 'PLUMCANDY X'

(50) Latin Name: ***Prunus* sp.**
Varietal Denomination: Plumcandy X

(76) Inventor: Lowell Glen Bradford, Le Grand, CA (US)

( * ) Notice: Subject to any disclaimer, the term of this patent is extended or adjusted under 35 U.S.C. 154(b) by 55 days.

(21) Appl. No.: 13/374,021

(22) Filed: Dec. 8, 2011

(51) Int. Cl.
*A01H 5/00* (2006.01)

(52) U.S. Cl.
USPC ..... Plt./180

(58) Field of Classification Search
USPC ..... Plt./180
See application file for complete search history.

(56) References Cited

U.S. PATENT DOCUMENTS

PP14,220 P2 10/2003 Bradford

*Primary Examiner* — Annette Para

(57) ABSTRACT

The present invention relates to an interspecific tree and more particularly to a new and distinct variety broadly characterized by a large size, medium vigorous, hardy, and very productive tree. Being self-unfruitful, the present variety requires cross pollination from an apricot, interspecific, or plum that blooms during the mid season. The fruit matures under the ecological conditions described during early September, with first picking on Sep. 8, 2011. The fruit is uniformly medium in size, full red in skin color, semi-clingstone in type, globose in shape, yellowish white in flesh color, firm in texture, and mildly sweet with a hint of coconut in flavor.

1 Drawing Sheet

Botanical classification: *Prunus* sp.
Varietal denomination: 'PLUMCANDY X'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'Plumcandy X'.

During a typical blooming season I isolate as seed parents both individual and groups of different plum trees by covering them with screen houses. A hive of bees is placed inside each such house, and bouquets to provide pollen from different plum, apricot, and interspecific hybrid trees are placed in buckets near the trees approximately every two days for the duration of the bloom. During 2001 one such house containing an unpatented red plum, code named '39P898', was crossed by me in this manner. To pollinate this red plum, I selected bouquets from several sources of apricot and interspecific hybrid trees without keeping specific written details. Upon reaching maturity the fruit from this red plum tree was harvested and the seeds were removed, cracked, stratified and germinated as a group with the label "H15B". They were grown as seedlings on their own root in my greenhouse and upon reaching dormancy transplanted to a cultivated area of my experimental orchard located near Le Grand, Calif. in Merced County (San Joaquin Valley). During the summer of 2005 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 39P898 plum (unpatented) by producing fruit that is firm, juicy, medium size, globose in shape and that matures in the late season, but is quite distinguished therefrom by producing fruit that is much sweeter, red instead of dark purple in skin color, and white instead of yellow in flesh color.

The present variety is most similar to 'September Yummy®' plum (U.S. Plant Pat. No. 14,220) by producing fruit that is full red in skin color, juicy, firm, globose in shape, semi-freestone in type, sweet in flavor, and mature in mid September, but is distinguished therefrom by producing fruit that is somewhat smaller in size, that is white instead of mostly yellow in flesh color, and that has a unique coconut tasting flavor.

SUMMARY OF VARIETY

The present interspecific variety is characterized by a large size, medium vigorous, hardy, and very productive tree. Being self-unfruitful, the present variety requires cross pollination from an apricot, interspecific, or plum that blooms during the mid season. The fruit matures under the ecological conditions described during early September, with first picking on Sep. 8, 2011. The fruit is uniformly medium in size, full red in skin color, semi-clingstone in type, globose in shape, yellowish white in flesh color, firm in texture, and mildly sweet with a hint of coconut in flavor.

DRAWING

The accompanying photograph consists of four whole fruits positioned to display the characteristics of the skin color and form, a half fruit sectioned to reveal the flesh and stone, typical leaves, and two insets depicting the flower buds and blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of firm ripe no Sep. 13, 2011, on the original tree during its tenth growing season. The flower and bud descriptions were developed during the previous blooming season. All major color code designations are by reference to the Inter-Society Color Council, National Bureau of Standards. Common color names are also used occasionally.

PARENTAGE

Seed parent: '39P898' plum (unpatented).
Pollen parent: Unknown.

TREE

Size: Large, reaching a height of 12' [3.66 m.] and a spread of 10' (3.05 m.) after ten growing seasons utilizing typical dormant pruning.

Vigor: Medium vigor, responding typically to irrigation and fertilization. The variety grows about 4' [1.22 m.] of surplus top-growth during the spring and summer. The plant should be grown on a standard commercial rootstock for production purposes.

Growth: Spreading to slightly drooping and dense.

Form: Pruned to a vase form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Vey production, thinning usually necessary.

Fertility: Self-unfruitful, requiring cross pollination by a suitable mid seasonal blooming apricot, interspecific, or plum, such as 'September Yummy®' plum (U.S. Plant Pat. No. 14,220).

Bearing: Regular bearer, no crop failures observed, weather dependent.

Trunk:

*Size*.—Medium, reaching a maximum diameter of 4⅞" [123.8 mm.] after the tenth growing season.

*Texture*.—Medium shaggy.

*Bark color*.—A Grayish yellowish brown [80. gy.yBr] and Dark yellowish brown [78. d.yBr] variegation with Light yellowish brown [76. l.yBr] crevices present.

*Lenticels*.—Approximate Number Per Square Inch: 8. Color: Brownish orange [54. brO]. Average Size: 5/16" [7.9 mm.]. Shape: Elongated, eye-shaped.

Branches:

*Size*.—Limb diameter is 3⅛" [79.4 mm.] measured 12" above the crotch, 1⅞" [47.6 mm.] measured 12" above the first fork.

*Texture*.—Smooth on first year wood, increasing roughness with age.

*Color*.—1st Year Wood Topside: Grayish red [19. gy.R]. 1st Year Wood Underside: Brilliant yellow green [116. brill.YG]. 2nd Year Wood: A Strong brown [55. s.Br] and Grayish brown [61. gy.Br] variegation.

*Lenticels*.—Number Per Square Inch: About 60 on second year wood. Color: Dark orange yellow [72. d.OY]. Average Size: 1/32" [0.8 mm.]. Shape: Elongated, eye-shaped.

Leaves:

*Size*.—Medium. Average Length: 3⅜" [85.7 mm.]. Average Width: 1¾" [44.5 mm.].

*Arrangement*.—Alternate.

*Thickness*.—Medium.

*Form*.—Elliptical.

*Apex*.—Acuminate.

*Base*.—Acute to rounded, with an average base angle of 70 degrees.

*Surface*.—Smooth.

*Color*.—Dorsal Surface: Moderate olive green [125. m.OlG]. Ventral Surface: Moderate yellow green [120. m.YG].

*Margin*.—Finely serrate.

*Venation*.—Pinnately net veined.

*Petiole*.—Average Length: ½" [12.7 mm.]. Average Thickness: 1/16" [1.6 mm.]. Color: Light yellow green [119. l.YG] with some Moderate yellowish pink [29. m.yPk] areas where exposed to strong sunlight.

*Stipules*.—Number: Usually 2 per leaf, up to 6 per growing tip. Average Length: 7/16" [11.1 mm.]. Color: Brilliant yellow green [116. brill.YG].

*Glands*.—Number: Mostly 2 per leaf. Position: Mostly alternately positioned on petiole near the intersection of the petiole and the base of the leaf blade. Size: Medium. Form: Globose. Color: Light yellow green [119. l.YG] acquiring Dark yellowish brown [78. d.yBr] centers with age. Leaf buds: Pointed, medium.

Flower buds:

*Hardiness*.—Hardy, with respect to central California winters.

*Diameter*.—Typically 3/16" [4.8 mm.] 1 week before bloom.

*Length*.—Typically ⅜" [9.5 mm.] 1 week before bloom.

*Form*.—Not appressed.

*Surface*.—Pubescent.

*Tip color*.—White [263. White].

Flowers: Perfect, complete, perigynous, usually a single pistil, typically thirty or more stamens, five sepals and petal locations alternately positioned.

*Average flower diameter*.—15/16" [23.8 mm.].

*Number of petals*.—Five, no double blossoms observed.

*Petal shape*.—Oval to circular.

*Petal margin*.—Entire, smooth to slightly wavy.

*Average petal diameter*.—7/16" [11.1 mm.].

*Average petal length*.—9/16" [14.3 mm.].

*Petal apex*.—Rounded.

*Petal base*.—Obtuse.

*Petal color*.—White [263. White] on both sides.

*Anther color*.—Strong orange yellow [68. s.OY].

*Stigma color*.—Brilliant greenish yellow [98. brill.gY].

*Sepal color*.—Light yellow green [119. l.YG] on the outer surface, Light grayish red [18. l.gy.R] around the outer edges on some.

*Sepal length*.—3/16" [4.8 mm.].

*Sepal width*.—5/32" [4.0 mm.].

*Sepal apex*.—Rounded to elliptical to match the width and length.
*Sepal margin*.—Fairly smooth, with slight serrations toward the apex.
*Average pistil length*.—½" [12.7 mm.].
*Average stamen length*.—7/16" [11.1 mm.].
*Fragrance*.—Moderate.
*Pollen production*.—Abundant, extremely bee enticing.
*Bloom density*.—Heavy.
*Number per cluster*.—2 to 8, average 3.
*Blooming period*.—Medium, three days after 'Black Amber' plum (unpatented).
*Onset of bloom*.—One percent on Feb. 28, 2011.
*Date of full bloom*.—Mar. 7, 2011.
*Duration of bloom*.—One to two weeks, dependent on ambient temperature.

FRUIT

Maturity when described: Firm ripe, Sep. 13, 2011.
Date of first picking: Sep. 8, 2011.
Date of last picking: Sep. 22, 2011.
Size: Uniform, medium.
*Average diameter axially*.—2 7/16" [61.9 mm.].
*Average diameter across cheek plane*.—2½" [63.5 mm.].
*Average diameter across suture plane*.—2⅜" [60.3 mm.].
*Typical weight*.—4.9 ounces [138.9 grams].
Form: Uniform, globose, symmetrical.
*Longitudinal section form*.—Round to slightly oval.
*Transverse section through diameter*.—Round.
Suture: An inconspicuous line located in a medium groove extending from the base just to the pistol point.
Ventral surface: Rounded, lightly lipped throughout.
Lips: Mostly equal.
Cavity: Flaring, circular, suture showing on one side.
*Depth*.—⅜" [9.5 mm.].
*Breadth*.—15/16" [23.8 mm.].
Base: Truncate, cordate if viewed parallel to the suture.
Apex: Rounded, slightly cordate if viewed parallel to the suture.
Pistil point: An inconspicuous Grayish yellowish brown [80. gy.yBr] dot located at the end of the suture.
Stem: Medium.
*Average length*.—⅜" [9.5 mm.].
*Average width*.—3/32" [2.4 mm.].
Skin:
*Thickness*.—Medium.
*Surface*.—Smooth.
*Tenacity*.—Tenacious to the flesh.
*Astringency*.—Nonastringent.
*Tendency to crack*.—None observed.
*Color*.—Very deep red [14. v.deep R] over a Very red [11. v.R] background with Moderate orange yellow [71. m.OY] freckling throughout.
*Bloom*.—Abundant.
Flesh:
*Color*.—Yellowish white [92. yWhite] throughout.
*Surface of pit cavity*.—Covered with Yellowish white [92. yWhite] broken fibers when twisted away from stone.
*Amygdalin*.—Slight.
*Juice*.—Moderate, rich.
*Texture*.—Firm, tough, meaty.
*Fibers*.—Abundant, fine.
*Ripens*.—Fairly even, slightly earliest toward the apex.
*Flavor*.—Mildly sweet, very distinct with a hint of coconut, typically 18 to 20 brix.
*Aroma*.—Very slight.
*Eating quality*.—Very good.

STONE

Type: Semi-free.
Form: Oval.
Hilum: Narrow to slightly oblong.
Base: Cordate.
Apex: Acuminate.
Sides: Equal.
Surface: Rough throughout with furrows on each side of the dorsal fin.
External Color of Stone: Light yellowish brown [76. l.yBr] when first removed.
Pit wall color when cracked: Dark orange yellow [72. d.OY].
Cavity surface color: Strong yellowish brown [74. s.yBr].
Average pit wall thickness: 1/16" [1.6 mm.].
Average width: ⅝" [15.9 mm.].
Average length: 13/16" [20.6 mm.].
Average breadth: 13/32" [10.3 mm.].
Tendency to split: None observed.
Kernel:
*Form*.—Oval.
*Skin color*.—Dark orange yellow [72. d.OY] when first removed.
*Pellicle color*.—Dark yellowish brown [78. d.yBr].
*Vein color*.—Moderate yellowish brown [77. m.yBr].
*Taste*.—Slightly bitter.
*Viable*.—Yes.
*Average width*.—7/16" [11.1 mm.].
*Average length*.—⅝" [15.9 mm.].
*Amygdalin*.—Moderate.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is most similar to 'September Yummy®' plum (U.S. Plant Pat. No. 14,220) by producing fruit that is full red in skin color, juicy, firm, globose in shape, semi-freestone in type, sweet in flavor, and that matures in mid September, but is distinguished therefrom by producing fruit that is somewhat smaller in size, that is white instead of mostly yellow in flesh color, and that has a unique coconut tasting flavor.

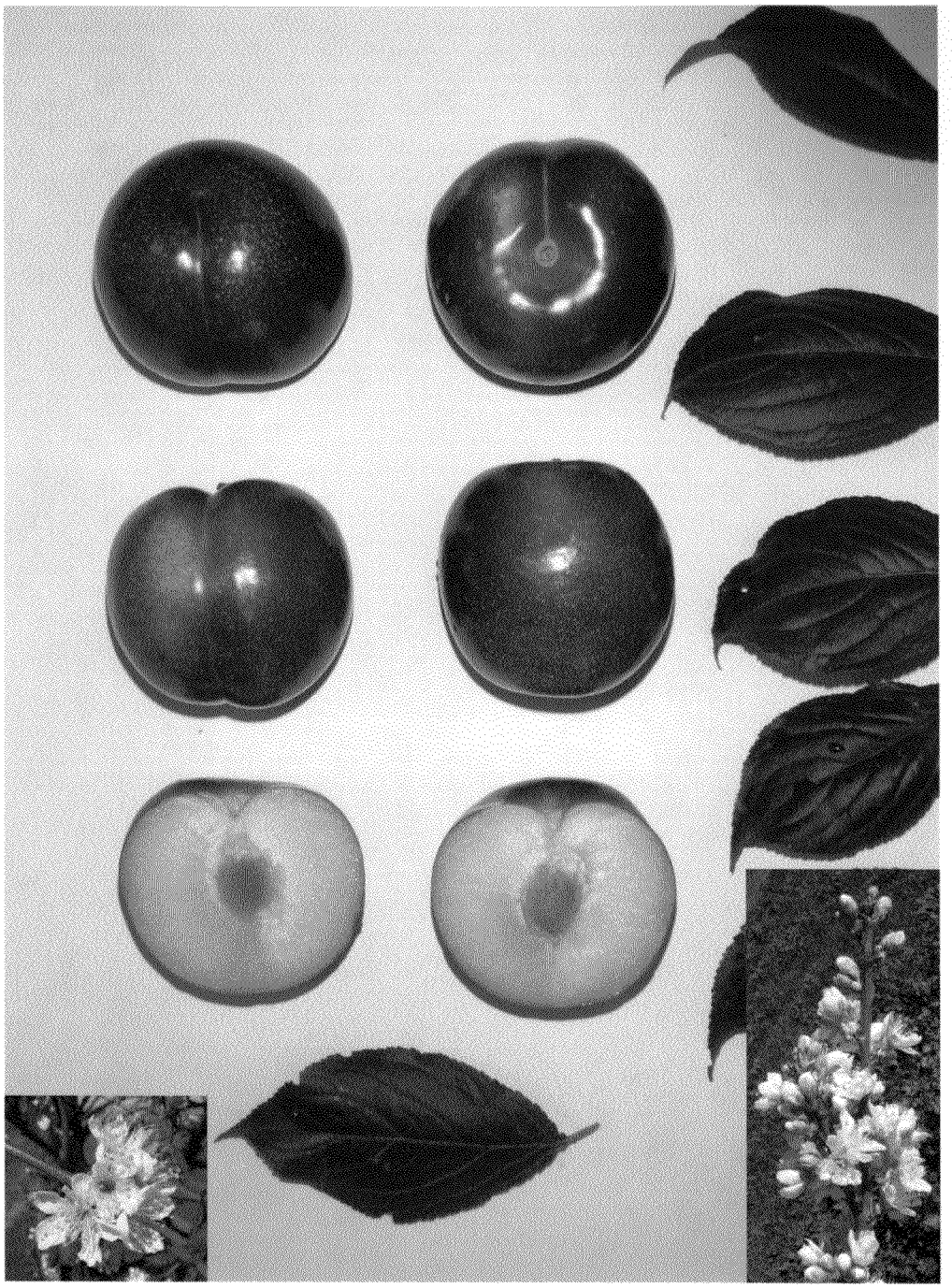

* * * * *